US009833405B2

(12) United States Patent
Xu et al.

(10) Patent No.: US 9,833,405 B2
(45) Date of Patent: Dec. 5, 2017

(54) BIODEGRADABLE MICRODEPOT DELIVERY SYSTEM FOR TOPICAL DELIVERY

(71) Applicant: Nano and Advanced Materials Institute Limited, Hong Kong (HK)

(72) Inventors: Jinjie Xu, HK (HK); Ho Wang Tong, HK (HK); Sau Kuen Connie Kwok, HK (HK); Ngar Yee Huen, HK (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 0 days.

(21) Appl. No.: 14/656,711

(22) Filed: Mar. 13, 2015

(65) Prior Publication Data

US 2015/0265530 A1 Sep. 24, 2015

Related U.S. Application Data

(60) Provisional application No. 61/967,455, filed on Mar. 19, 2014.

(51) Int. Cl.
*A61K 9/00* (2006.01)
*A61K 47/38* (2006.01)
(Continued)

(52) U.S. Cl.
CPC .......... *A61K 9/0021* (2013.01); *A61K 31/455* (2013.01); *A61K 38/06* (2013.01);
(Continued)

(58) Field of Classification Search
None
See application file for complete search history.

(56) References Cited

U.S. PATENT DOCUMENTS 7,615,234 B2 11/2009 Potter et al.
2011/0045041 A1 * 2/2011 Golubovic-Liakopoulos ............................ A61K 8/0208 424/401

(Continued)

FOREIGN PATENT DOCUMENTS

CN 103402496 A 11/2013
CN 103816611 A 5/2014
WO 2013/057918 A1 4/2013

OTHER PUBLICATIONS

Lee et al., "Dissolving microneedles for transdermal drug administration prepared by stepwise controlled drawing of maltose", Biomaterials, 32, pp. 3134-3140 (2011).*
Mei-Chin Chen, Ming-Hung Ling, Kuan-Ying Lai, and Esar Pramudityo. "Chitosan Microneedle Patches for Sustained Transdermal Delivery of Macromolecules", Biomacromolecules 2012, 13, 4022-4031.
Henry S, McAllister D V, Allen M G, et al. "Microfabricated microneedles: a novel approach to transdermal drug delivery", Journal of pharmaceutical sciences, 1998, 87(8): 922-925.
Sullivan S P, Murthy N, Prausnitz M R. "Minimally invasive protein delivery with rapidly dissolving polymer microneedles", Advanced Materials, 2008, 20(5): 933-938.
Wang P M, Cornwell M, Hill J, et al. "Precise microinjection into skin using hollow microneedles", Journal of investigative dermatology, 2006, 126(5): 1080-1087.

(Continued)

*Primary Examiner* — Bethany Barham
*Assistant Examiner* — Barbara Frazier
(74) *Attorney, Agent, or Firm* — Spruson & Ferguson (HK)

(57) ABSTRACT

The present invention provides a biodegradable microdepot delivery system for topical delivery of active ingredients through the skin surface of a subject. The configuration, dimension, and chemical composition of the microdepots allow a relatively short dissolution time of less than 5 minutes while insertion ratio of the microdepots can reach more than 60%, some of which can even reach about 97%, under exertion of a relatively low pressing force. The present invention also provides a method for fabricating the biodegradable microdepot delivery system and a polymeric solution for forming the same.

27 Claims, 8 Drawing Sheets

Complete degradation with needle-free waste

Drug-loaded MN patch

Macromolecular drugs

Applying to the skin

Drug release through swelling and degradation of MNs

(51) Int. Cl.

| | |
|---|---|
| ***A61K 38/06*** | (2006.01) |
| ***A61K 38/08*** | (2006.01) |
| ***A61K 31/455*** | (2006.01) |
| ***A61K 47/32*** | (2006.01) |
| ***A61K 47/36*** | (2006.01) |

(52) U.S. Cl.
CPC .............. *A61K 38/08* (2013.01); *A61K 47/38* (2013.01); *A61K 47/32* (2013.01); *A61K 47/36* (2013.01)

(56) References Cited

U.S. PATENT DOCUMENTS

| | | | | |
|---|---|---|---|---|
| 2011/0177297 A1* | 7/2011 | Jung | .................... | A61K 9/0021 428/172 |
| 2012/0028947 A1* | 2/2012 | Xia | ...................... | A61K 9/0048 514/179 |

OTHER PUBLICATIONS

Ling MH, Chen MC. "Dissolving polymer microneedle patches for rapid and efficient transdermal delivery of insulin to.diabetic rats" Acta Biomater 2013, 9(11):8952-8961.

Lee JW, Choi SO, Felner El, Prausnitz MR. Dissolving microneedle patch for transdermal delivery of human growth hormone. Small. 2011, 7(4):531-539.

Office Action issued from the State Intellectual Property Office of the People's Republic of China dated Apr. 27, 2017.

* cited by examiner (A)

Before dissolution 5 min 15 min 30 min (B)

60 min (A)

Before dissolution 5 min (B)

15 min 30 min 60 min (A)

(B)

(A)

(B)

BIODEGRADABLE MICRODEPOT DELIVERY SYSTEM FOR TOPICAL DELIVERY

CROSS REFERENCE TO RELATED APPLICATION

Pursuant to 35 U.S.C. §119(e), this is a non-provisional patent application which claims benefit from U.S. provisional patent application Ser. No. 61/967,455 filed Mar. 19, 2014, and the disclosure of which is incorporated herein by reference in its entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to a delivery system for topical delivery of active ingredients to the skin of a subject. In particular, the present invention provides a delivery system as a patch which is biodegradable in a relatively shorter period of time for topical delivery of active ingredients to the skin of the subject. The present invention also relates to a method for fabricating the delivery system and a composition forming the same.

BACKGROUND

Conventional means for topical delivery of active ingredients to the skin of a recipient is mainly based on microneedle technology. There are two major limitations in the current microneedle's development: 1) in academic research, most published studies focused on the delivery of macromolecules (e.g. vaccines, insulin) using microneedles, in which many applications however are not explored especially in skin care; 2) On the other hand, microneedle therapy system (MTS) has recently become a fashionable beauty treatment, in which a device, usually in the form of a roller or stamp with many fine needles is used to create micro-channels in the skin prior to the further treatment. However, the increased risks of microbial infection due to the reused microneedles and biohazardous sharps left in the skin after use limit its applications and popularity. As such, a biodegradable microdepot system with the capacity of effective penetration while providing sustained active release in one single step could be an alternative to the conventional means based on the microneedle technology.

In U.S. Pat. No. 7,615,234, a method of delivering at least one therapeutic compound or a formulation comprising the same is disclosed, where a pioneer projectile in different dimensions and shapes is used in that method. Although the pioneer projectile in '234 appears to be biodegradable, a driving force is required to inject the therapeutic compound or formulation through the penetration of the projectile into the skin. It is not convenient for consumers who may not have enough skills to handle injection needle. There is also a risk of losing control when exerting too much force onto the therapeutic compound or formulation based on the method of '234. The injection mechanism for introducing the projectile to penetrate through the skin is somehow an invasive approach which may also be at risk of physically damaging skin tissue during the injection process.

In Henry et al. (1998), it disclosed a metallic microneedle assay which was pressed into epidermis using a force of about 10 N applied with a small wooden probe (2 mm in diameter; Baxter Healthcare, Round Lake, Ill.). To better simulate the in vivo mechanical environment, the dermis was placed below the epidermis as a supporting cushion. Insertion of the arrays into skin required only gentle pushing (estimated to be approximately 10 N, which is about the force needed to push an elevator button). After the microneedles were inserted, the epidermis and microneedles were inspected by light (StereoZoom 7; Bausch & Lomb, Rochester, N.Y.) and/or scanning electron (S-800, Hitachi, Tokyo, Japan) microscopy. FIG. 1 shows the microneedle tips inserted across epidermis. An array of microneedles was inserted into the stratum corneum side of human epidermis. The underside of the epidermis is shown, indicating that the microneedles penetrated across the tissue and that the tips were not damaged. Arrows indicate some of the microneedle tips. Inspection by light and electron microscopy showed that more than 95% of microneedles within an array pierced across the stratum corneum of the epidermis samples. However, such microneedle tips are invasive and difficult to handle by consumers in general. Fabrication thereof and in most conventional transdermal delivery means involve the use of acid which may cause side effect to the user such as allergy or actual skin damage.

To meet the need for a delivery system which is safe and reliable, an active ingredient-loaded transdermal delivery system with sufficient penetration efficiency while biodegradable at a certain time period is desired.

SUMMARY OF THE INVENTION

Accordingly, the first aspect of the present invention relates to a biodegradable microdepot delivery system for topical delivery of active ingredients. The system of the present invention basically comprises an array of microdepots supported by a base. In one embodiment, the system of the present invention can be a patch. In another embodiment, each of the microdepots has an aseptic ratio from 1 to 10. In other embodiment, the microdepot has an aseptic ratio of 2. In yet another embodiment, the microdepot has a height from 300 to 600 μm and a base width from 150 to 300 μm. Each microdepot can be cone-shaped, pyramid-shaped or bevel-angled. The system of the present invention is polymer-based and the polymer(s) used to fabricate the system is/are biodegradable within certain period of time. In one embodiment, the present system can be degraded within 60 minutes after being exposed to a skin surface. In another embodiment, the present system is degradable within 15 minutes after being exposed to the skin surface. In other embodiment, the microdepots are degraded faster than the base of the present system after being exposed to the skin surface. The insertion efficiency of the present system is more than 60%. In one embodiment, the present system can reach the insertion efficiency of more than 60% when it is pressed towards the skin surface using a force of as low as 0.3N.

The second aspect of the present invention relates to a method for fabricating the biodegradable microdepot delivery system of the present invention. The method comprises (a) providing a mould for forming a microdepot template; (b) forming a microdepot template corresponding to the mould and fixing the template at a centre of a centrifuge holder; (c) adding a polymeric solution to one surface of the template for forming the biodegradable microdepot delivery system; (d) centrifuging at a speed by a centrifuge for certain period of time at certain temperature such that the polymeric solution is centrifuged down to a plurality of wells on said surface of the template; (e) repeating steps (c) and (d) for at least 4 times; and (f) drying the template with the polymeric solution for at least 1 day to form the biodegradable microdepot delivery system. In one embodiment, the number of wells to be formed on said surface of the microdepot template is 100 where each of the longitudinal and lateral axes of the template contains 10 wells. In another embodiment, tip-to-tip distance between two wells (no matter between two wells on the same longitudinal axis or lateral axis) is between 500 and 600 μm. According to an embodiment of the present invention, the microdepot template is in a form of an array with a surface area of 1 $cm^2$ (dimension: 1 cm×1 cm). In other embodiment, each of the microdepots to be formed in the microdepot delivery system by the present method has an aseptic ratio from 1 to 10. In yet another embodiment, the microdepot of the microdepot delivery system formed by the present method has an aseptic ratio between 2 and 3. In a further embodiment, the microdepot of the microdepot delivery system formed by the present method has a height from 300 to 600 μm and a base width from 150 to 300 μm. Each microdepot of the microdepot delivery system formed by the present method can be cone-shaped, pyramid-shaped or bevel-angled, in accordance with the shape and dimension of the well on said surface of the microdepot template, i.e., corresponding to the shape and dimension of microdepot on said mould for forming the microdepot template. According to an embodiment of the present invention, the polymeric solution to be added to one surface of the microdepot template is at least 100 μl for each time. In one embodiment, the volume of the polymeric solution to be added to one surface of the microdepot template is from 100 to 200 μl each time. In another embodiment, the volume of the polymeric solution to be added to one surface of the microdepot template is about 100 μl each time. According to an embodiment of the present invention, the centrifuge is set at a speed from 4,500 to 7,500 rpm and for 10 to 60 minutes at a temperature from 20° C. to 30° C. to centrifuge the polymeric solution added to said surface of the microdepot template. In one embodiment, the speed of the centrifuge is set at 4,680 rpm. In another embodiment, the time for centrifugation is for 30 minutes. In other embodiment, the temperature during centrifugation is 25° C. Said adding of the polymeric solution to said surface of the microdepot template and centrifuging thereof by said centrifuge at the speed for the period of time at the temperature as specified in one of the embodiments of the present invention are repeated for 4 to 6 times until all the wells of the template are filled up with the polymeric solution and a thin layer of the polymeric solution covers said surface of the template. In one embodiment, said adding and centrifuging are repeated for 6 times. The thin layer will become a base of the microdepot delivery system of the present invention after said drying. In one embodiment, the base of the microdepot delivery system of the present invention is about 100 μm in thickness. Such thickness can ensure good handling property of the microdepot while minimal amount of materials is consumed. According to an embodiment of the present invention, said drying is for 1 to 4 days. In one embodiment, said drying is for 2 to 4 days. In another embodiment, said drying is for 1 to 2 days.

The third aspect of the present invention relates to a polymeric solution for forming the biodegradable microdepot delivery system of the present invention. The polymeric solution of the present invention comprises one or more biodegradable polymers, a glycosaminoglycan, a polysaccharide, and a cellulose derivative. In one embodiment, the one or more biodegradable polymers comprise different polyvinylpyrrolidone (PVP) in different molecular weights. The polyvinylpyrrolidone (PVP) of the polymeric solution can be in a molecular weight ranging from 10,000 to 90,000. In another embodiment, the PVP of the polymeric solution comprises PVP with an average molecular weight of 10,000, 30,000 and/or 90,000. In a preferred embodiment, the PVP of the polymeric solution comprises PVP 10, Povidone K30, and/or Povidone K90. Also in a preferred embodiment, the glycosaminoglycan of the polymeric solution is hyaluronic acid (HA); the polysaccharide of the polymeric solution is dextran 70; the cellulose derivative of the polymeric solution is sodium carboxymethyl cellulose (CMC). In an exemplary embodiment, the polymeric solution comprises 20-100% v/v HA, 5-40% v/v dextran 70. 1-20% v/v Povidone K30, 1-20% v/v Povidone K90, 1-20% v/v PVP 10, and 5-30% v/v CMC. In a preferred embodiment, the weight ratio of HA:dextran 70:Povidone K90 is 9-11:10-8:1 and the total concentration of HA, dextran 70 and Povidone K90 is 50% by volume of the polymeric solution. In a more preferred embodiment, the weight ratio of HA:dextran 70:Povidone K90 is 9:10:1. The polymeric solution of the present invention further comprises one or more active ingredients to be incorporated into the microdepot delivery system of the present invention for topical application. The one or more active ingredients are macromolecules comprising amides and peptides for skin care or medication. In one embodiment, the one or more active ingredients comprise Niacinamide, Pal-KTTKS and GHK-Cu. In another embodiment, the polymeric solution of the present invention comprises 2-10% w/v Niacinamide, 2-15% w/v Pal-KTTKS, and/or 0.2-15% w/v GHK-Cu. In a preferred embodiment, Niacinamide is in a concentration of about 2%; Pal-KTTKS is in a concentration of 3-10%; GHK-Cu is in a concentration of 0.2-5%

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

Figure 1:
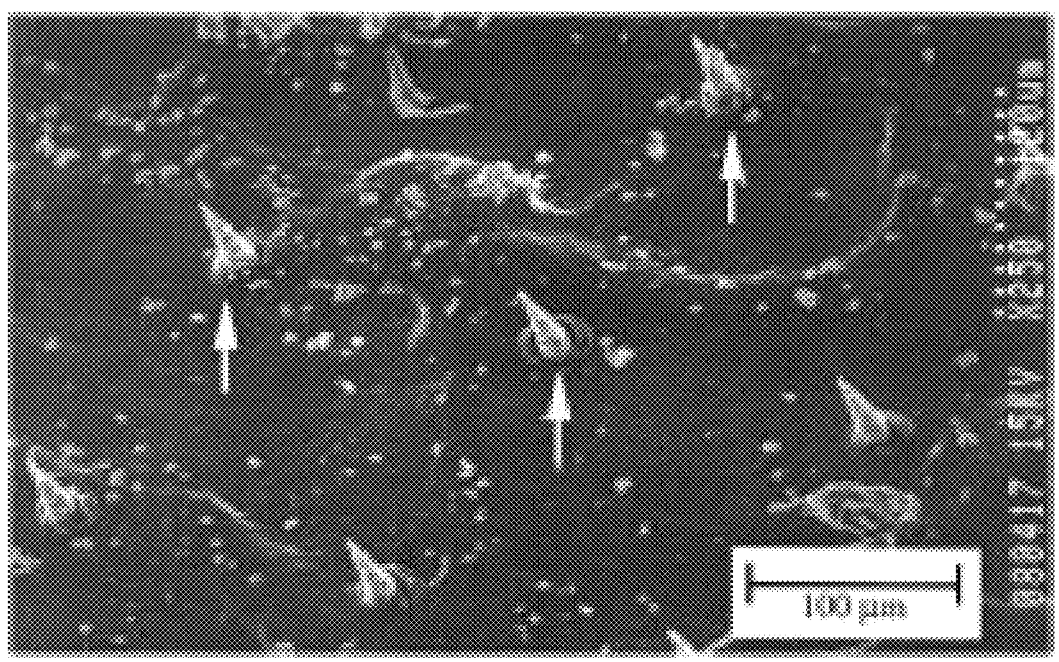
FIG. 1 shows microneedle tips inserted across epidermis, where the result is from a prior art.

The following description and the corresponding embodiments of the present invention are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

EXAMPLES

Example 1—Cell Viability Assay (MTT) for In Vitro Skin Irritation of Active Ingredients of the Microdepot Delivery System of the Present Invention 1.1 Materials and Method HaCaT cells, a human keratinocyte cell line, are used as the in vitro model to test any irritation effect of the active ingredients used in the polymeric solution to form the microdepot delivery system of the present invention. The following is the procedures of an MTT assay for testing any skin irritation effect of the active ingredients used in the polymeric solution of the present invention:

a) 12 mM MTT stock solution is prepared by adding 1 mL of sterile PBS into one 5 mg vial of MTT (Component A) and mixed by sonication until the vial of MTT is dissolved in the PBS;
b) HaCaT cells at 5,000 cells per well are seed into a 96-well plate and incubated at 37° C. in 5% $CO_2$ for 24 to 48 hours until the cells become adherent;
c) Culture medium in each well is removed and replaced with 100 μL of test compound (e.g., active ingredient used in the polymeric solution of the present invention);
d) 10 μL of the MTT stock solution prepared in step (a) is added to each well; a negative control containing 100 μL of culture medium and 10 μL of the MTT stock solution is also included for comparison;
e) Both test samples and negative control prepared in step (d) are incubated at 37° C. for 4 hours;
f) 25 μL of the solution is removed from each well after incubation in step (e) followed by adding 50 μL of DMSO to each well and mix thoroughly by pipette;
g) The mixture in step (f) is incubated at 37° C. for 10 minutes;
h) The mixture in each well after the incubation in step (g) is mixed again before measuring absorbance at 540 nm;
i) The mixture is subject to a spectrophotometer to measure the absorbance at 540 nm.

The cell viability of HaCaT cells with the treatment of the test compound is calculated based on the following formula:

$$\text{Cell viability} = \frac{OD_{④} - OD_{③}}{OD_{②} - OD_{①}} \times 100\%$$

where $OD_{①}$ is the absorbance of culture medium only; $OD_{②}$ is the absorbance of the culture medium with the cells; $OD_{③}$ is the absorbance of the culture medium with the test compound; and $OD_{④}$ is the absorbance of the culture medium with the cells and test compound.

1.2 Results

The results of the MTT assay and cell viability calculated based on the formula in this example are shown in Table 1.

TABLE 1

| | Niacinamide 2% | Niacinamide 4% | Niacinamide 6% | Niacinamide 8% | Niacinamide 10% | Normal Control |
|---|---|---|---|---|---|---|
| OD560 | 1.412 | 1.122 | 0.951 | 1.033 | 0.9877 | 1.228 |
| Cell viability(%) | 115 | 91.34 | 77.44 | 84.08 | 80.43 | 100 |
| | Pal-KTTKS 3% | Pal-KTTKS 4% | Pal-KTTKS 5% | Pal-KTTKS 8% | Pal-KTTKS 10% | |
| OD560 | 1.461 | 1.659 | 1.506 | 1.743 | 1.57 | |
| Cell viability(%) | 119 | 135.1 | 122.6 | 141.9 | 127.8 | |
| | GHK-Cu 0.2% | GHK-Cu 0.5% | GHK-Cu 1% | GHK-Cu 2% | GHK-Cu 5% | |
| OD560 | 1.66 | 1.718 | 1.775 | 1.629 | 1.671 | |
| Cell viability(%) | 135.1 | 139.6 | 144.6 | 132.7 | 136.1 | |

The results in Table 1 show that none of the active ingredients cause any significant cell death in the skin cell line. If the viability of an active ingredient of a certain concentration is higher than or equal to that of the control, it is assumed that the active ingredient at that concentration is non-cytotoxic. It can be seen from the results in Table 1 that the peptide Pal-KTTKS with concentrations ranging from 3% to 10% are non-cytotoxic. It can also be seen from Table 1 that the peptide GHK-Cu with concentrations ranging from 0.2% to 5% are non-cytotoxic. Niacinamide at 2% can also be regarded as non-cytotoxic.

Example 2—Fabrication of Microdepot Array

Figure 3:
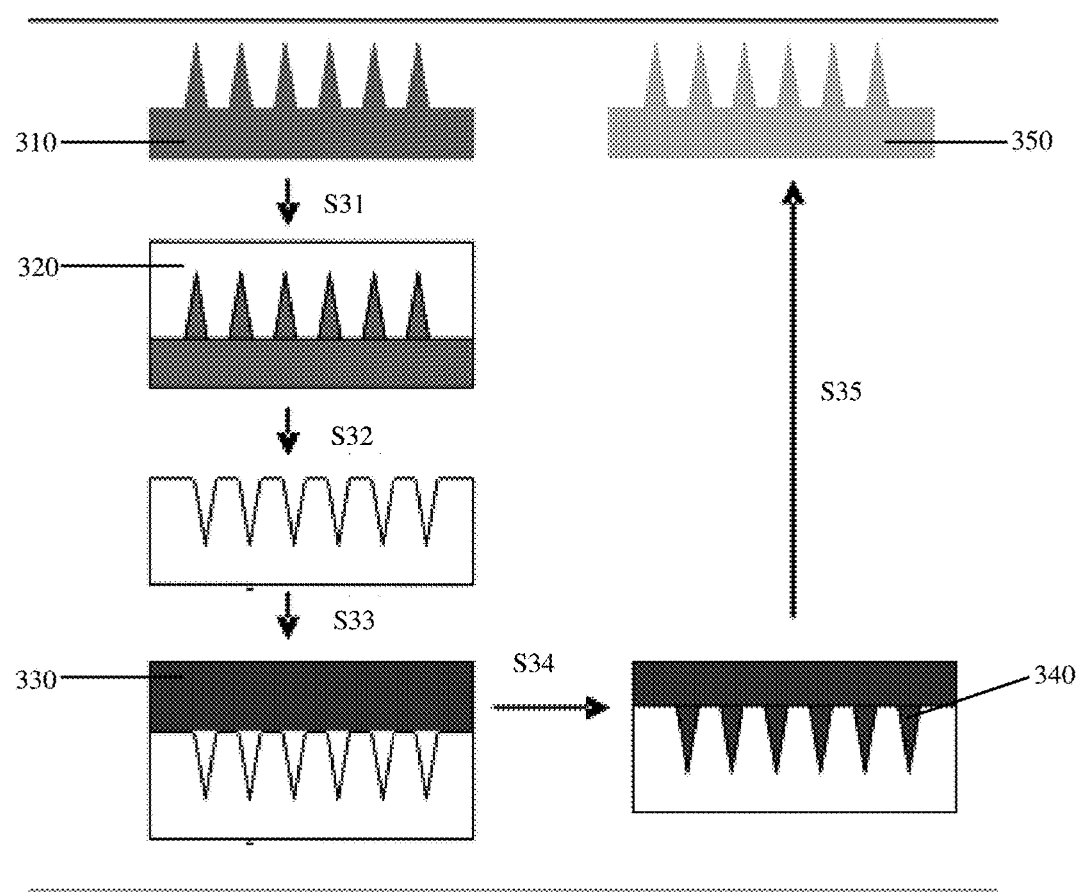
FIG. 3 is a flow diagram depicting the method for fabricating the microdepot delivery system according to an embodiment of the present invention.

The microdepot delivery system of the present invention is fabricated according to the following procedures which are depicted in FIG. 3:

(a) Providing a mould (310) for forming a microdepot template (S31);

(b) Forming a microdepot template (320) corresponding to the mould (310) and fixing the template at the centre of a centrifuge holder (S32);

(c) Adding a polymeric solution to one surface of the template (330) for forming the biodegradable microdepot delivery system (S33);

(d) Centrifuging at a speed by a centrifuge for certain period of time at certain temperature such that the polymeric solution is centrifuged down to a plurality of wells (340) on said surface of the template (S34);

(e) Repeating steps (c) and (d) for at least 4 times (not shown in FIG. 3); and (f) Drying the template with the polymeric solution for at least 1 day to form the biodegradable microdepot delivery system in array form (350) (S35).

Since active ingredients are intended to be encapsulated in the tip of the microdepot, the active ingredients should be incorporated during the first time of casting, i.e., the active ingredients should be mixed with the first batch of polymeric solution being added and then centrifuged down to the plurality of wells in steps (S33) and (S34).

According to the method described in this example, the number of wells to be formed on said surface of the microdepot template is 100 where each of the longitudinal and lateral axes of the template contains 10 wells. Tip-to-tip distance between two wells (no matter between two wells on the same longitudinal axis or lateral axis) is between 500 and 600 μm. The microdepot template is in a form of an array with a surface area of 1 $cm^2$ (dimension: 1 cm×1 cm). Each of the microdepots to be formed in the microdepot delivery system by the present method has an aseptic ratio from 1 to 10. The aseptic ratio of each microdepot in this example is 2. Also, the microdepot formed in this example has a height from 300 to 600 μm and a base width from 150 to 300 μm. Each microdepot formed by the present method can be cone-shaped, pyramid-shaped or bevel-angled, in accordance with the shape and dimension of the well on said surface of the microdepot template, i.e., corresponding to the shape and dimension of microdepot on said mould for forming the microdepot template. Table 2 shows the configuration of different dimensions of the microdepot according to the parameters described in this example:

TABLE 2

Configuration of Different Microdepot Patches

| Microdepot per array | Height (μm) | Base (μm) | Tip-to-Tip distance (μm) | Array Area ($cm^2$) |
|---|---|---|---|---|
| 10 × 10 | 450 | 150 | 500 | 1 |
| 10 × 10 | 600 | 300 | 600 | 1 |
| 10 × 10 | 600 | 150 | 600 | 1 |
| 10 × 10 | 300 | 150 | 600 | 1 |

Figure 2:
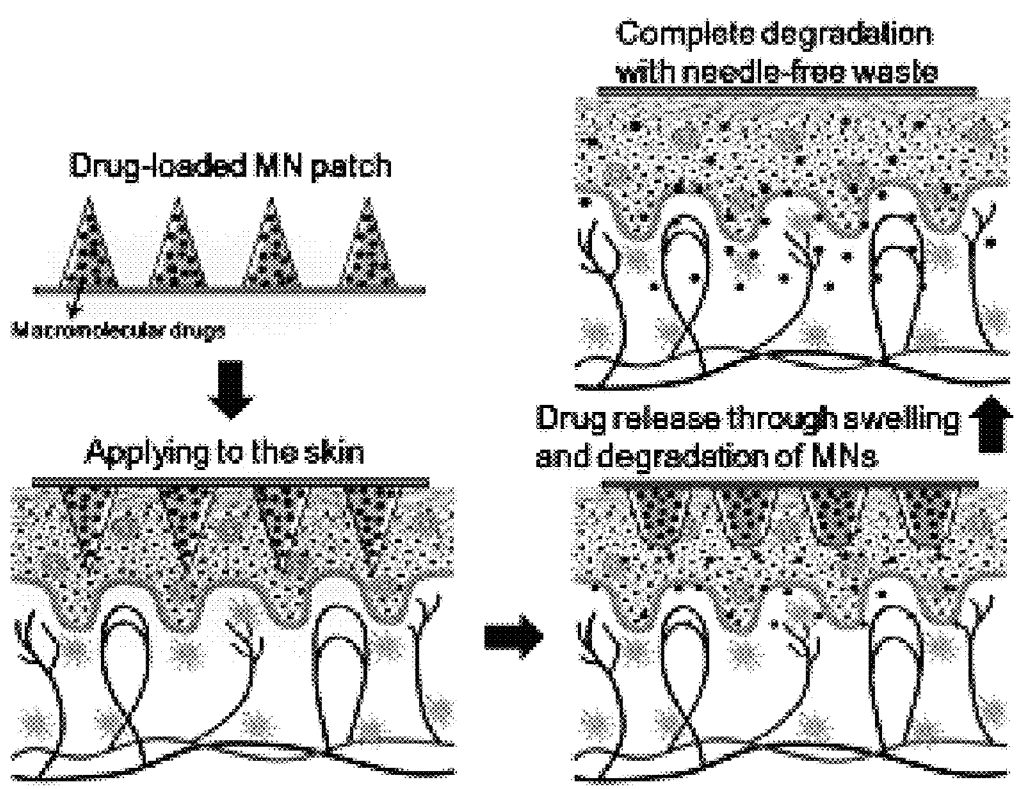
FIG. 2 is a schematic diagram depicting how the microdepot delivery system of the present invention delivers macromolecules to the skin of a subject.

Based on the configuration set forth in Table 2, the volume of the polymeric solution to be added to one surface of the microdepot template is about 100 μl each time. Also, the speed of the centrifuge used in this example is at 4,680 rpm, the time for centrifugation is for 30 minutes, and the temperature during centrifugation is 25° C. The steps of adding the polymeric solution to said surface of the microdepot template and centrifuging thereof by said centrifuge at the speed for the period of time at the temperature as specified in this example are repeated for 6 times. The thin layer will become a base of the microdepot delivery system of the present invention after drying. The thickness of the base of the microdepot delivery system is as thin as possible, e.g., 100 μm. The microdepot array in this example is dried in air for 1 to 2 days. After that, the dried microdepot array can be ready for topical application. A schematic diagram of how this microdepot array is used as a patch to deliver the pre-loaded active ingredients to the skin of a subject (e.g. human) is shown in FIG. 2.

Example 3—Mechanical Strength Test of Microdepot Delivery System

The microdepot delivery system in array form in various dimensions prepared according to the foregoing examples is subject to mechanical tests for compression, dissolution kinetics and skin insertion.

In this example, the maximum bending strength of the microdepot array is tested with a constant force. The constant force applied in the test is in a range from 0.5N to 15N/array Porcine cadaver skin (area=1.5 cm×1.5 cm) is used as a model to mimic human skin and applied thereon the microdepot array in different dimensions for incubation and photographs are taken at different time intervals (e.g., 5, 15, 30, 60 minutes, respectively) under the exertion of the constant force. After removal of the microdepot array, the microdepot array is immediately observed using inverted fluorescence microscope. The porcine cadaver skin is kept warmed at 37° C. in a beads bath in this example. Different compositions of the polymeric solution to form the microdepot and configurations of the microdepot array under this test are shown in Table 3. Four different compositions of the polymeric solution, namely MH-1, MH-2, MH-3 and MH-4, are used to form the microdepot array, and two different configurations, i.e., 450 μm×150 μm (Height×Width), 10×10 array; and 600 μm×300 μm (Height×Width), 10×10 array, are applied on the porcine cadaver skin.

TABLE 3

| | Composition of Polymeric Solution | | | |
|---|---|---|---|---|
| Dimension | MH-1 | MH-2 | MH-3 | MH-4 |
| 450 μm × 150 μm (Height × Width), 10 × 10 array | 20% Hyaluronic acid | — | — | — |
| 600 μm × 300 μm (Height ×Width), 10 × 10 array | — | 50% Hyaluronic acid | 100% Hyaluronic acid | Hyaluronic acid: Dextran 70: Povidone K90 = 11:8:1; total concentration: 50% |

Figure 4:
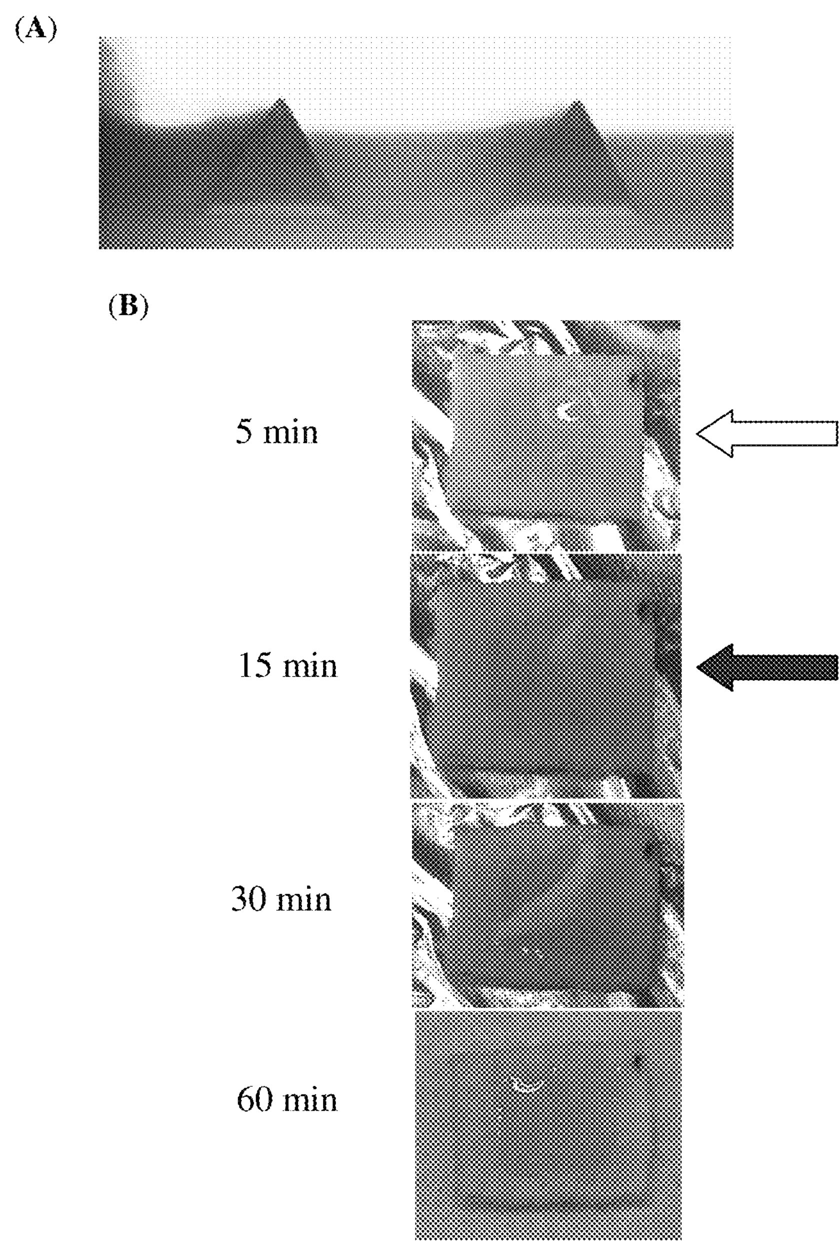
FIG. 4 shows photographs taken by inverted fluorescence microscope of the microdepot array formed by a polymeric solution according to an embodiment of the present invention: (A) side view of the array before dissolution; (B) top view of the porcine cadaver skin inserted with the microdepot array (contains 20% HA) for 5 minutes, 15 minutes, 30 minutes and 60 minutes, respectively; unshaded arrow indicates the photograph showing complete dissolution of the microdepots; shaded arrow indicates the photograph showing complete dissolution of the base of the microdepot array.

FIG. 4A shows a side view under inverted fluorescence microscope before dissolution (at time=0 minute) of the microdepot formed by MH-1 (comprising 20% hyaluronic acid) and in a configuration of 450 μm×150 μm (Height×Width) for each microdepot with 10×10 microdepots per array. At 0 minute, the microdepot formed by MH-1 is substantially in triangular shape from the side view under the microscope. FIG. 4B is a series of photographs taken in 5 minutes, 15 minutes, 30 minutes and 60 minutes, from the bottom side of the base of the microdepot array formed by the MH-1 and applied with constant force (e.g., 0.3N) pressing towards the porcine cadaver skin. In FIG. 4B, the microdepots are shown to be completely dissolved while the base of the microdepot array is partially dissolved in about 5 minutes after applying the microdepot array on the porcine cadaver skin (indicated by un-shaded arrow) under exertion of the constant force. The microdepot assay is completely dissolved in 15 minutes after applying which on the porcine cadaver skin (indicated by shaded arrow).

Figure 5:
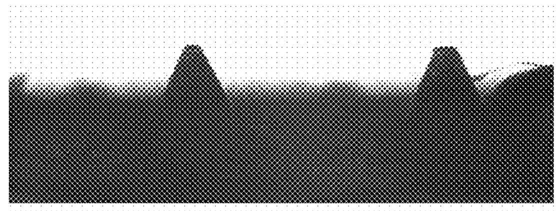
FIG. 5 shows photographs taken by inverted fluorescence microscope of the microdepot array formed by a polymeric solution according to an embodiment of the present invention: (A) side view of the array before dissolution, inserted for 5 minutes, 15 minutes, and 30 minutes, respectively; (B) top view of the porcine cadaver skin inserted with the microdepot array (contains 50% HA) for 60 minutes; unshaded arrow indicates the photograph showing complete dissolution of the microdepots; shaded arrow indicates the photograph showing complete dissolution of the base of the microdepot array.
Figure 5:
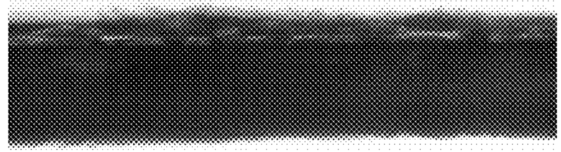
Figure 5:
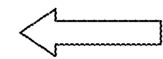
Figure 5:
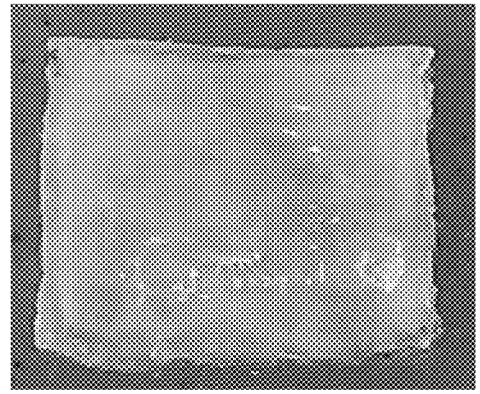

FIG. 5A shows a series of photographs taken from the side view under the inverted fluorescence microscope before dissolution (at time=0 minute), in 5 minutes, 15 minutes and 30 minutes under the application of constant force (e.g., 0.3N) on the base of the microdepot array formed by MH-2 (comprising 50% hyaluronic acid) and in a configuration of 600 μm×300 μm (Height×Width) for each microdepot with 10×10 microdepots per array. The microdepot formed by MH-2 is also substantially in triangular shape from the side view under the microscope. FIG. 5B shows a photograph taken from the bottom side of the base of the microdepot array formed by MH-2 and applied with the force pressing towards the porcine cadaver skin for 60 minutes. The microdepots of the microdepot array formed by MH-2 are completely dissolved in 15 minutes (indicated by unshaded arrow) and the base thereof is completely dissolved in 60 minutes (indicated by shaded arrow) after applying the same on the porcine cadaver skin.

Figure 6:
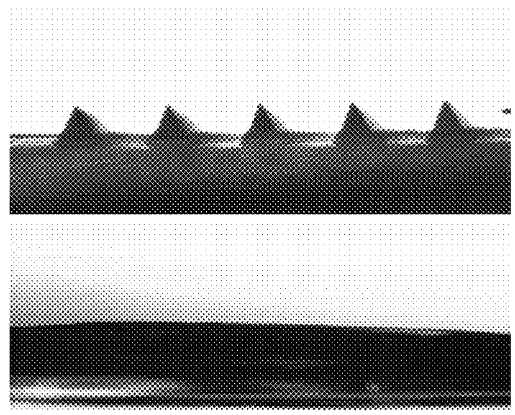
FIG. 6 shows photographs taken by inverted fluorescence microscope of the microdepot array formed by a polymeric solution according to an embodiment of the present invention: (A) side view of the array before dissolution and being inserted for 5 minutes, respectively; (B) top view of the porcine cadaver skin inserted with the microdepot array (contains 100% HA) for 15 minutes, 30 minutes and 60 minutes; unshaded arrow indicates the photograph showing complete dissolution of the microdepots; shaded arrow indicates the photograph showing complete dissolution of the base of the microdepot array.
Figure 6:
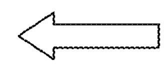
Figure 6:
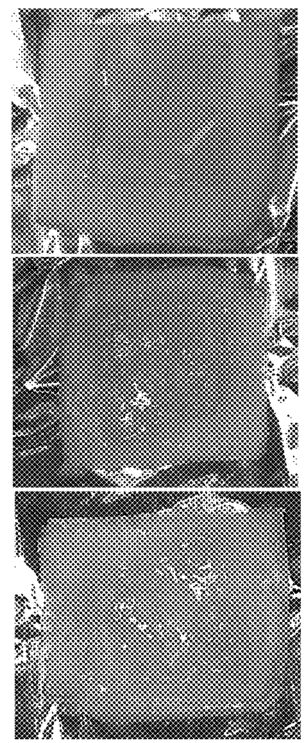
Figure 6:
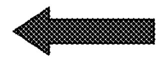

FIG. 6A shows photographs taken under the inverted fluorescence microscope from the side view of the microdepot array formed by MH-3 (comprising 100% hyaluronic acid) and in a configuration of 600 μm×300 μm (Height×Width) for each microdepot with 10×10 microdepots per array being applied on the porcine cadaver skin with the exertion of constant force (e.g., 0.3N) pressing towards the porcine cadaver skin from the top of the microdepot array. In FIG. 6A, the upper photograph shows that the microdepot array remains intact and the microdepot is substantially in triangular shape at 0 minutes while the lower photograph shows that the microdepots are completely dissolved in 5 minutes after applying the microdepot array formed by MH-3 on the porcine cadaver skin under exertion of the constant force. FIG. 6B is a series of photographs taken from the bottom side of the base of the microdepot array applied on the porcine cadaver skin for 15 minutes, 30 minutes and 60 minutes, respectively under exertion of the constant force. In the upper photograph of FIG. 6B, the base of the microdepot array is completely dissolved in 15 minutes. In the middle and lower photographs of FIG. 6B, the microdepot array is substantially invisible and only the porcine cadaver skin is visible after the microdepot array is applied on the porcine cadaver skin for 30 minutes or more under exertion of the constant force.

Figure 7:
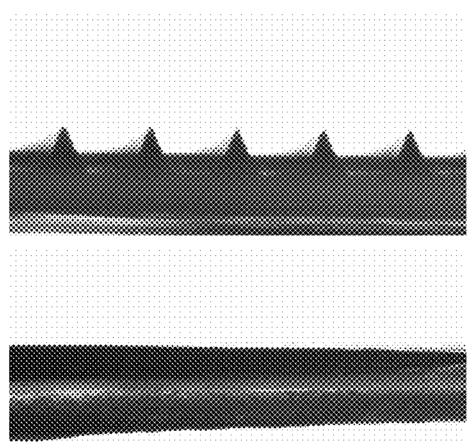
FIG. 7 shows photographs taken by inverted fluorescence microscope of the microdepot array formed by a polymeric solution according to an embodiment of the present invention: (A) side view of the array before dissolution and being inserted for 5 minutes, respectively; (B) top view of the porcine cadaver skin inserted with the microdepot array (contains 11:8:1 in weight ratio of HA:Dextran 70:Povidone K90) for 15 minutes, 30 minutes and 60 minutes; unshaded arrow indicates the photograph showing complete dissolution of the microdepots; shaded arrow indicates the photograph showing complete dissolution of the base of the microdepot array.
Figure 7:
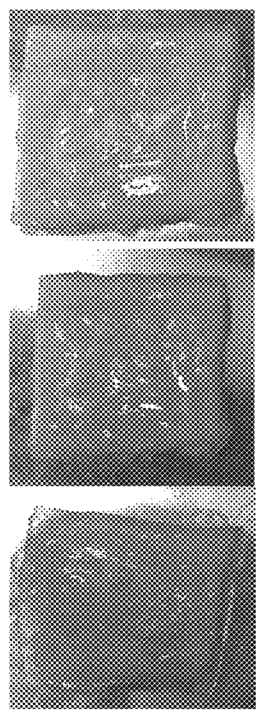

FIG. 7A shows photographs taken under the inverted fluorescence microscope from the side view of the microdepot array formed by MH-4 (comprising hyaluronic acid, dextran 70 and Povidone K90 in weight ratio of 11:8:1, where the total concentration of these three components is about 50%) and in a configuration of 600 μm×300 μm (Height×Width) for each microdepot with 10×10 microdepots per array being applied on the porcine cadaver skin with exertion of the constant force (e.g., 0.3N) pressing towards the porcine cadaver skin from the base of the microdepot array. The upper photograph in FIG. 7A shows that the microdepots remain substantially in triangular shape at 0 minutes while the lower photograph in FIG. 7A shows that microdepots are completely dissolved in 5 minutes after applying the same on the porcine cadaver skin under exertion of the constant force. In FIG. 7B, the upper photograph taken from the top view of the microdepot array shows that the base of the microdepot array is completely dissolved. The middle and lower photographs in FIG. 7B taken from the top of the microdepot array after applying the same on the porcine cadaver skin for 30 and 60 minutes, respectively, show that the microdepot array is substantially invisible while only the porcine cadaver skin is visible under the microscope.

Collectively, from the results in this example, the dissolution time of the microdepot patch should be <60 minutes. The hyaluronic acid is preferred to be 20% v/v or more (up to 100%) in the polymeric solution forming the microdepot delivery system of the present invention such that the dissolution time for the whole array (including the base) can be completely dissolved within 15 minutes after applying the array on the skin under exertion of the constant force as low as 0.3N. In this example, the microdepots formed by all compositions of the polymeric solution can be completely dissolved in 5 minutes or less.

Example 4—Skin Insertion Test

In this example, trypan blue stain is used to visualize the number of microdepots inserted into the porcine cadaver skin using a constant force in order to determine the insertion ratio of the microdepot delivery system of the present invention into the skin. Trypan blue stain is incorporated into the microdepot array during fabrication according to the dimensions and compositions of the polymeric solution described in Example 3 and some other compositions as shown in Table 4. The constant force applied towards the bottom side of the base of the microdepot array is as low as 0.3N for 5 minutes in a bead bath at 37° C. To facilitate the test, a handheld syringe-type applicator is used to exert the force. In application, no syringe or syringe-type applicator is required. After pressing the microdepot array on the porcine cadaver skin for 5 minutes under the exertion of the constant force, the microdepot array is removed from the porcine cadaver (if it is not completely dissolved) and the residual dye is removed from the skin surface by dry paper. After removing the residual dye from the skin surface, Auto Fine-Focus Digital Microscope is used to calculate the insertion ratio (number of spots stained with trypan blue/number of microdepots in the microdepot array×100%) of the microdepot array. In the present invention, insertion ratio of >60% is desired.

TABLE 4

| | Name of Different Compositions of Polymeric Solution | | | | | | | | |
|---|---|---|---|---|---|---|---|---|---|
| | MH-1 | MH-2 | MH-3 | MH-4 | P5 | P6 | P7 | P8 | P9 |
| Composition of Key Components | 20% HA | 50% HA | 100% HA | HA:Dextran 70:Povidone K90 = 11:8:1 (by wt.) | PVP 10:Dextran 70 = 4:1 (by wt.) | Dextran 70:Povidone K90 = 4:1 (by wt.) | Dextran 70:Povidone K90 = 9:1 (by wt.) | Dextran 70:Povidone K90 = 3:2 (by wt.) | HA/Dextran 70:Povidone K90 = 9:10:1 (by wt.) |
| Height × Base Width (μm) | 450 × 150 | 600 × 300 | 600 × 300 | 600 × 300 | 600 × 300 | 600 × 300 | 600 × 300 | 600 × 300 | 600 × 300 |
| Aspect Ratio | 3 | 2 | 2 | 2 | 2 | 2 | 2 | 2 | 2 |
| Dissolution time (<60 minutes) | ✓ | ✓ | ✓ | ✓ | X | X | X | ✓ | ✓ |
| Insertion ratio (>60%) | — | — | 96% (n = 2) | 86% (n = 4) | 81% (n = 3) | 83% (n = 4) | 86% (n = 4) | 93% (n = 4) | 95% (n = 4) |

NB: "HA": hyaluronic acid;
"—": not tested or below 60% insertion ratio

Figure 8:
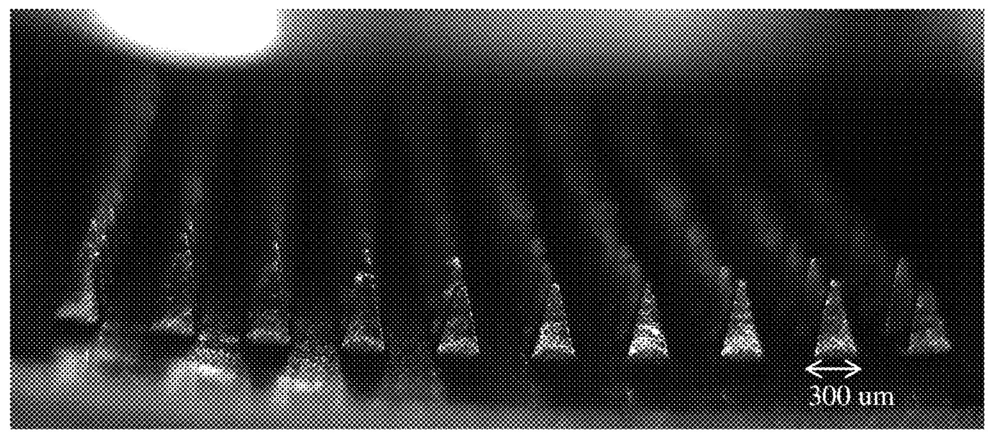
FIG. 8 shows micrographs to indicate blue tissue dye-loaded microdepot array formed by a polymeric solution according to an embodiment of the present invention (contains 100% HA) before insertion (A) and after insertion and removal from the porcine cadaver skin (B).
Figure 8:
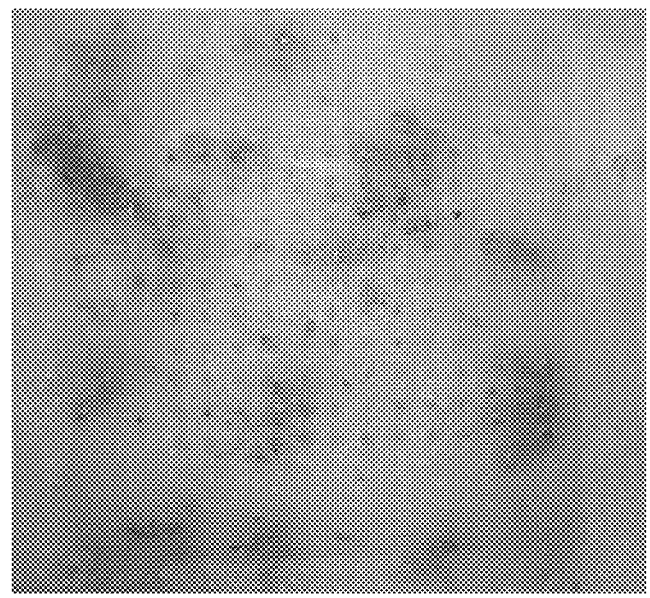

From the results as shown in Table 4 and FIG. 8, it is demonstrated that the insertion ratios are higher than 95% in both MH-3 (~96%) and P9 (~95%); the third among the these in this example is the array formed by P8 (93%). It is noteworthy that the microdepot arrays formed by MH-1 and MH-2 are difficult to be demolded from the template during fabrication while the microdepot arrays formed by P5 to P7 do not reach the dissolving time of within 60 min. The performance of MH-3 and P9 is similar, however, adding Dextran 70 and Povidone K90 instead of Hyaluronic acid alone can reduce the cost. In summary, the results in Table 4 shows that the microdepot array formed by P9 (with the weight ratio of HA:Dextran 70:Povidone K90=9:10:1) is the most preferable according to the insertion ratio and also the dissolution time. In FIG. 8A, as long as the dimension of the microdepot is the same, even the composition of the polymeric solution is changed into HA:Dextran 70:Povidone K90 in 9:10:1 instead of 100% HA, the shape of the microdepot is more or less the same. FIG. 8B shows that the microdepots formed by MH-3 are also mostly inserted into the porcine cadaver skin, by the blue stain remaining into the skin.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to better explain the principles of the invention and its practical application, thereby enabling others skilled in the art to understand the invention for various embodiments and with various modifications that are suited to the particular use contemplated. It is intended that the scope of the invention be defined by the following claims and their equivalence.

REFERENCES

The following references are incorporated herein by reference in their entirety:

1. Henry S, McAllister D V, Allen M G, et al. Microfabricated microneedles: a novel approach to transdermal drug delivery[J]. Journal of pharmaceutical sciences, 1998, 87(8): 922-925.

What is claimed is:

1. A polymeric solution for forming an array of microdepots of a biodegradable microdepot delivery system, said polymeric solution comprising one or more biodegradable polymers, a glycosaminoglycan, and a polysaccharide, the weight ratio of glycosaminoglycan:polysaccharide:biodegradable polymer is 9-11:10-8:1; said one or more biodegradable polymers is Povidone K90; said polysaccharide is dextran 70; said glycosaminoglycan is hyaluronic acid and wherein the total concentration of Povidone K90, dextran 70 and hyaluronic acid is 50% by volume of the polymeric solution.

2. The solution of claim 1, wherein the glycosaminoglycan of the polymeric solution is hyaluronic acid (HA) ranging from 22.5-27.5% v/v.

3. The solution of claim 1, wherein the polysaccharide of the polymeric solution is dextran 70 ranging from 20-25% v/v.

4. The solution of claim 1, further comprising sodium carboxymethyl cellulose (CMC) ranging from 5 to 30% v/v.

5. The solution of claim 1, further comprising one or more active ingredients comprising amides and peptides.

6. The solution of claim 5, wherein the one or more active ingredients comprise 2% w/v Niacinamide, 3-10% w/v Pal-KTTKS, and/or 0.2-5% w/v GHK-Cu.

7. The solution of claim 1, wherein the weight ratio of glycosaminoglycan:polysaccharide:biodegradable polymer is 9:10:1.

8. A biodegradable microdepot delivery system for topical delivery of active ingredients comprising an array of microdepots formed by the polymeric solution of claim 1 and a base supporting said array, each microdepot having an aseptic ratio from 1 to 10, a height from 300 to 600 μm and a base width from 150 to 300 μm, each microdepot being either cone-shaped, pyramid-shaped or bevel-angled, the array being degraded within 60 minutes after being exposed to a skin surface using a force of as low as 0.3N and having an insertion efficiency of more than 60%.

9. The system of claim 8, wherein said array has one hundred microdepots on the surface opposite to the base in a configuration of 10×10 microdepots in a surface area of 1 $cm^2$.

10. The system of claim 8, wherein each microdepot of said array incorporates at least one active ingredient to be delivered to the skin surface.

11. The system of claim 8, wherein a tip-to-tip distance between two microdepots is from 500 to 600 μm.

12. The system of claim 8, wherein the aseptic ratio is between 2 and 3.

13. The system of claim 10, wherein said at least one active ingredient comprises amides and peptides.

14. The system of claim 10, wherein said at least one active ingredient comprises Niacinamide, Pal-KTTKS and GHK-Cu.

15. The system of claim 8, wherein said base has a thickness of about 100 μm.

16. A method for fabricating the biodegradable microdepot delivery system of claim 8, said method comprising:

(a) providing a mould for forming a microdepot template;

(b) forming a microdepot template corresponding to the mould and fixing the template at a centre of a centrifuge holder;

(c) adding a polymeric solution to one surface of the template for forming the biodegradable microdepot delivery system;

(d) centrifuging at a speed by a centrifuge for certain period of time at certain temperature such that the polymeric solution is centrifuged down to a plurality of wells on said surface of the template;

(e) repeating steps (c) and (d) for at least 4 times; and (f) drying the template with the polymeric solution for at least 1 day to form the biodegradable microdepot delivery system.

17. The method of claim 16, wherein the number of wells to be formed on said surface of the microdepot template is 100 where each of the longitudinal and lateral axes of the template contains 10 wells.

18. The method of claim 16, wherein a tip-to-tip distance between two wells is from 500 to 600 μm.

19. The method of claim 16, wherein the microdepot template is in a form of an array with a surface area of 1 $cm^2$.

20. The method of claim 16, wherein the volume of the polymeric solution to be added to one surface of the microdepot template is from 100 to 200 μl each time.

21. The method of claim 16, wherein the centrifuge is set at a speed from 4,500 to 7,500 rpm for 10 to 60 minutes at a temperature from 20° C. to 30° C. to centrifuge the polymeric solution added to said surface of the microdeport template.

22. The method of claim 21, wherein the speed of the centrifuge is set at 4,680 rpm.

23. The method of claim 21, wherein the time for centrifugation is for 30 minutes.

24. The method of claim 21, wherein the temperature during centrifugation is 25° C.

25. The method of claim 16, wherein steps (c) and (d) are repeated for 4 to 6 times until all the wells of the template are filled up with the polymeric solution and a thin layer of the polymeric solution covers said surface of the template.

26. The method of claim 16, wherein said drying is for 1 to 4 days.

27. The method of claim 16, wherein one or more active ingredients comprising 2% w/v Niacinamide, 3-10% w/v Pal-KTTKS, and/or 0.2-5% w/v GHK-Cu are mixed with the polymeric solution before said adding the polymeric solution to one surface of the template for forming the biodegradable microdepot delivery system in step (c).

* * * * *